US006852706B1

(12) United States Patent
Heber-Katz

(10) Patent No.: US 6,852,706 B1
(45) Date of Patent: Feb. 8, 2005

(54) METHODS AND COMPOSITIONS FOR HEALING HEART WOUNDS

(75) Inventor: Ellen Heber-Katz, Philadelphia, PA (US)

(73) Assignee: The Wistar Institute, Philadelphia, PA (US)

( * ) Notice: Subject to any disclaimer, the term of this patent is extended or adjusted under 35 U.S.C. 154(b) by 0 days.

(21) Appl. No.: 09/813,930

(22) Filed: Mar. 22, 2001

Related U.S. Application Data

(60) Provisional application No. 60/191,104, filed on Mar. 22, 2000.

(51) Int. Cl.[7] .......................... A01N 43/04; A61K 31/70
(52) U.S. Cl. ............................. 514/50; 514/1; 514/824
(58) Field of Search ....................................... 514/50, 2

(56) References Cited

FOREIGN PATENT DOCUMENTS

WO          97 33980 A      9/1997

OTHER PUBLICATIONS

Rosenbaum et al. American Heart Journal, Oct. 1983, vol. 106, No. 4, pp. 957–964.*
Ahmad et al. Cardiovascular Drugs and Therapy, 1995, vol. 9, pp. 827–828.*
Refetoff et al. The Consequences of Inappropriate Treatment Because of Failure to Recognize The Syndrome of Pituitary and Peripheral Tissue Resistance to Thyroid Hormone. Metabolism: Clinical and Experimental. Aug. 1983, vol. 32, No. 8.*
Loos et al. T3–Hyperthyroidism Cuased by Enhanced ans Shifted T4–Conversion. Hormone and metabolic Research. Supplement !984, vol. 14, pp. 85–93.*
Alain et al. Short Stature and Thyroxine–Binding Globulin Excess: Improvement With Triiodothyronine Treatment. Pediatrics vol. 81, No. 5, May 1988, pp. 674–679.*
Chappel et al. Relationship between thyroid function and cardiotoxic proprties of isoproterenol. Endocrinology, Aug. 1959, vol. 65, pp. 208–215.*
Treadwell et al. Successful Treatment of Recurrent Non–immune Hydrops Secondary to Fetal Hyperthyroidism. Obstetrics and Gynecology. May 1996, vol. 87, No. 5, part 2, pp. 838–840.*
Corte et al. Ischemia miocardia acuta in corso di tireotossicosi: regressione rapida dell'ischemia con l'impiego di propanololo e propiltiouracile. Gazz Med Ital. Arch. Sci. Med. 1993; 152: 149–53.*

Alpert et al. A myothermal analysis of the myosin cross-bridge cycling rate during isometric tetanus in normal and hypothyroid rat hearts. European Heart Journal (1984) 5 (supplement F) pp. 3–11.*
Heber–Katz, Ellen, Abstract of NIH Grant No. 1 ROI A142395–01, obtained from the CRISP database available at <http://www.nih.gov>; Letter from Dorrette M. Finch, Director of Division of Research Documentation at NIH, stating that the abstract of NIH Grant No. 1 ROI A142395–01 was posted on the CRISP system on May 1, 1998.
McBrearty et al. "Genetic analysis of a mammalian wound–healing trait" Proc. Natl. Acad. Sci, USA vol. 95, pp. 11792–11797, Sep. 1998.
Clark et al. "A New Murine Model for Mammalian Wound Repair and Regeneration" Clinical Immunology and Immunopathology, vol. 88, No. 1, Jul. pp. 35–45, 1998.
Goss and Grimes "Epidermal Downgrowths in Regenerating Rabbit Ear Holes" J. Morph., 146: 533–542 (1975).
Lander & Kruglyak "Genetic Dissection of Complex Traits: Guidelines for Interpreting and Reporting Linkage Results" Nature Genetics, vol. 11, Nov. 1995, pp. 241–247.
Yu et al. "Differential Gene Expression in Healing Rat Corneal Epithelium" Investigative Ophthalmology and Visual Science, vol. 36, No. 10, 1995 pp. 1997–2007.
Fassler et al. "Differential Regulation of Fibulin, Tenascin–C, and Nidogen Expression During Wound Healing of Normal and Glucoccorticoid–Treated Mice" Experimental Cell Research, vol. 222, 1996, pp. 111–116.
Hirobe "Genetic Factors Controlling the Proliferative Activity of Mouse Epidermal Melanocytes During the Healing of Skin Wounds" Genetics, vol. 120, 1988 pp. 551–558.
Dietrich et al. "A Genetic Map of the Mouse with 4,006 Simple Sequence Length Polymorphisms" Nature Genetics, vol. 7, 1994, pp. 220–245.
Hubner et al. "Differential Regulation of Pro–Inflammatory Cytokines During Wound Healing in Normal and Glucocorticoid–Treated Mice" Cytokine, vol. 8, No. 7, 1996, pp. 548–556.

* cited by examiner

Primary Examiner—Sean McGarry
Assistant Examiner—Jon B. Ashen
(74) Attorney, Agent, or Firm—Banner & Witcoff, Ltd.

(57) ABSTRACT

Levels of thyroid hormone can be decreased in a mammal to increase healing of heart wounds. The increased wound healing includes rapid re-epithelialization and recovery of normal architecture and function relative to mammals who have not been treated according to the invention.

11 Claims, 6 Drawing Sheets

US 6,852,706 B1

METHODS AND COMPOSITIONS FOR HEALING HEART WOUNDS

This application claims the benefit of co-pending application Ser. No. 60/191,104 filed Mar. 22, 2000, which is incorporated herein by reference.

TECHNICAL FIELD OF THE INVENTION

This invention is related to the field of wound healing. More particularly, the invention is related to methods and compositions for enhancing wound healing in mammalian hearts.

BACKGROUND OF THE INVENTION

The biological response to tissue injury in higher organisms falls into two main categories: wound repair and regeneration (24). In amphibians, the form of wound healing seen is often epimorphic regeneration, where entire limbs can be reformed after amputation (24). In adult mammals, wound healing can involve wound repair or tissue regeneration, including the replacement of mature cells through cell proliferation (25) or replenishment of cells, but not organs, from immature stem cells (26, 27, 28). Complete wound healing, however, with perfect replacement of tissue and function, is typically not observed. Injuries to the central and peripheral nervous system, including optic nerve and spinal cord injuries, are especially refractory to healing. Thus, there is a need in the art for methods and compositions for enhancing wound healing in mammals.

SUMMARY OF THE INVENTION

It is an object of the invention to provide reagents and methods for increasing healing of a heart wound in a mammal. These and other objects of the invention are provided by one or more of the embodiments described below. One embodiment of the invention is a method of increasing healing of a heart wound in a mammal. An effective amount of a thyroid hormone-lowering agent is administered to a mammal in need thereof. Healing of a heart wound in the mammal is thereby increased relative to healing of a heart wound in a mammal to whom the thyroid hormone-lowering agent has not been administered.

Thus, the invention provides the art with methods and reagents for increasing heart wound healing in a mammal.

DETAILED DESCRIPTION OF THE INVENTION

Figure 1A:
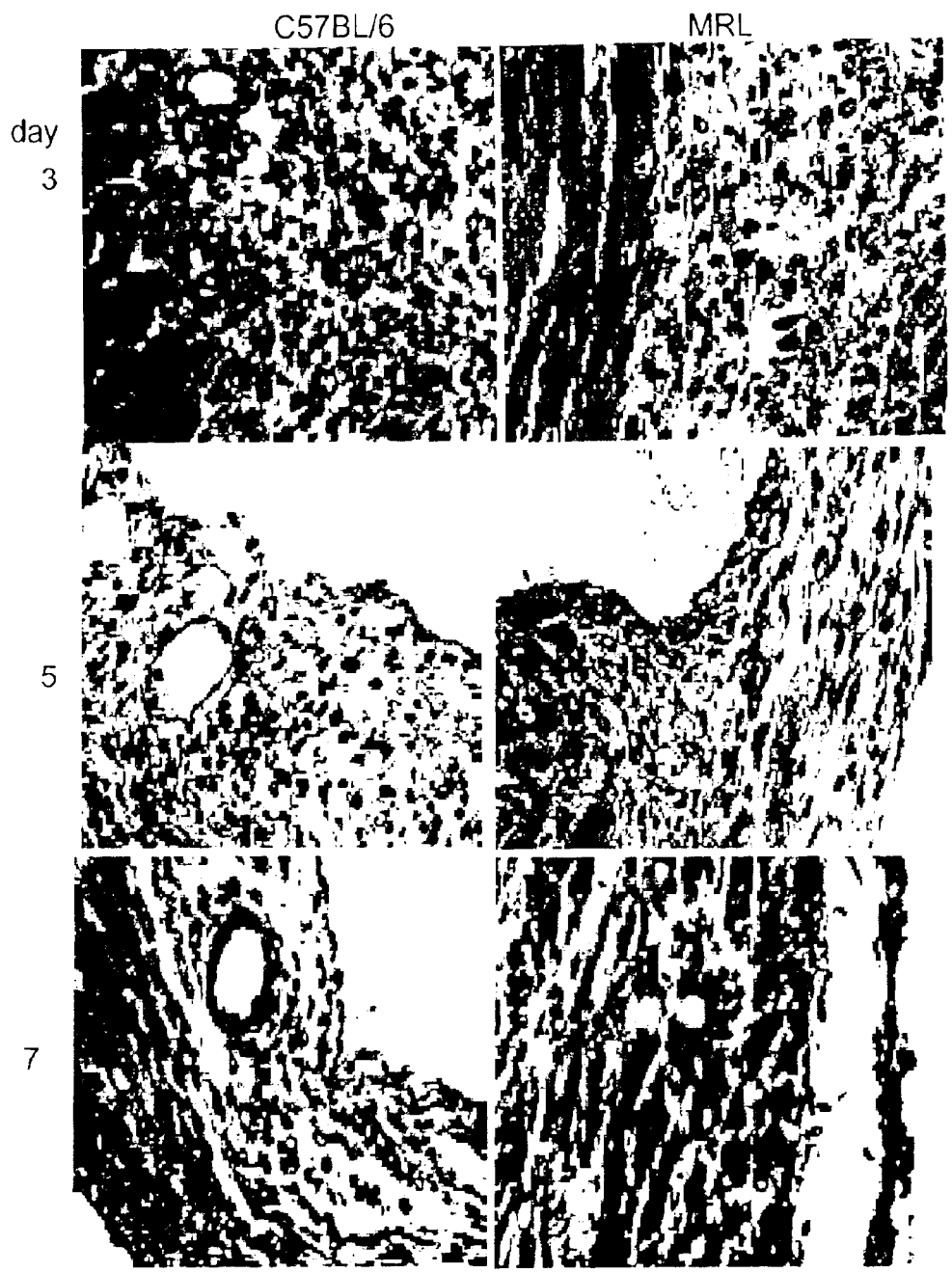
FIG. 1. Cardiac tissue from C57B1/6 and MRL mice was removed at various time points after cryo-injury and then fixed in Prefer solution, paraffin imbedded, sectioned and stained with trichrome. Lesions can be seen at days (FIG. 1A) 3, 5, and 15 (40×) and at day (FIG. 1B) 60 (4 & 40×).

It is a discovery of the present invention that lowering thyroid hormone levels increases wound healing, particularly heart wound healing. Increased wound healing according to the invention includes rapid re-epithelialization and recovery of normal architecture and function relative to wound healing in mammals which have not been treated according to the invention. Mammals whose wounds can be treated according to the invention include mice, dogs, cats, cows, horses, pigs, monkeys, and humans.

Wounds whose healing can be increased according to the invention include, but are not limited to, ischemic infarcts, surgical incisions, cuts, stretches, tears, pulls, abrasions, tissue punches, burns, bone breaks, crushes, scrapes, contusions, bruises, punctures, cold-induced lesions, and the like. Methods and compositions of the invention can be used to treat and thus increase healing of a wound by promoting processes such as angiogenesis, chondrogenesis, return of hair follicles and/or sebaceous glands, reepithelialization, rapid connective tissue proliferation, deposition of organized extracellular matrix, and restoration of normal tissue architecture and function. Surgical adhesions can be prevented by prophylactic treatment of surgical incisions using compositions and methods of the invention. These methods and compositions are useful in any situation in which regeneration or healing of a wound without formation of scar tissue is desired.

Thyroid hormone levels can be decreased prior to wounding, after wounding, or concomitant with wounding. Thyroid hormone levels (e.g., levels of T3 and/or T4) preferably are decreased by at least 10%, 25%, 50%, 60%, 70%, or 80% relative to thyroid hormone levels in a mammal which has not been treated according to the invention. Most preferably, thyroid hormone levels are decreased by at least 90%, 95%, 99%, or 100%.

Thyroid hormone levels can be decreased in a mammal by any method known in the art, including, but not limited to, administration of an effective amount of a thyroid hormone-lowering agent, such as propylthiouracil, methimazole, carbamizole, or radiolabeled iodide. Thyroid hormone levels also can be lowered by surgical removal of thyroid tissue. Partial or complete thyroidectomy can be performed.

In one embodiment, thyroid hormone levels are lowered by administering an antibody that specifically binds to thyroglobulin or to thyroid stimulating hormone. Antibodies which specifically bind to thyroglobulin or thyroid stimulating hormone, provide a detection signal at least 5-, 10-, or 20-fold higher than a detection signal provided with other proteins when used in Western blots or other immunochemical assays. Preferably, specific binding antibodies do not detect other proteins in immunochemical assays and can immunoprecipitate thyroglobulin or thyroid stimulating hormone from solution.

"Antibody" as used herein includes intact immunoglobulin molecules, as well as fragments thereof, such as Fab, $F(ab')_2$, and Fv, which are capable of binding an epitope of thyroglobulin or thyroid stimulating hormone. Antibodies can be purified by methods well known in the art. For example, the antibodies are affinity purified, by passing the antibodies over a column to which a wound healing protein is bound. The bound antibodies can then be eluted from the column, for example, using a buffer with a high salt concentration.

In another embodiment, the thyroid hormone-lowering agent is an antisense oligonucleotide which binds to thyroglobulin or to thyroid stimulating hormone mRNA to result in decreased thyroid hormone levels. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell using techniques well known in the art, such as transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

In another embodiment the thyroid hormone-lowering agent is a ribozyme which hybridizes to and cleaves an RNA sequence of a thyroglobulin or thyroid stimulating hormone mRNA (see Haseloff et al., U.S. Pat. No. 5,641,673).

A thyroid hormone-lowering agent can be present in a pharmaceutically suitable form, comprising a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles.

Pharmaceutically acceptable salts can also be used in wound healing compositions, for example, mineral salts such as hydrochlorides, hydrobromides, phosphates, or sulfates, as well as salts of organic acids such as acetates, proprionates, malonates, or benzoates. Wound healing compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a wound healing composition.

Administration of wound healing compositions of the invention can include local or systemic administration, including injection, oral administration, particle gun, or catheterized administration, and topical administration. For treatment of wounds on the surface of the body, a wound healing composition is typically prepared in a topical form, either as a liquid solution, suspension, gel, or cream. However, solid forms suitable for solution or suspension in liquid vehicles prior to injection can also be prepared, for local treatment of internal wounds. Both the dose of a particular wound healing composition and the means of administering the composition can be determined based on specific qualities of the wound healing composition, the condition, age, and weight of the patient, the type and extent of the wound being treated, and other relevant factors.

The above disclosure generally describes the present invention, and all patents and patent applications cited in this disclosure are expressly incorporated herein. A more complete understanding can be obtained by reference to the following specific examples which are provided for purposes of illustration only and are not intended to limit the scope of the invention.

EXAMPLE 1

Materials and Methods

Mice. The MRL/Mp+/+ ("healer") mouse was obtained from the Jackson Laboratory (Bar Harbor, Me.) and the C57BL/6 ("nonhealer") control strain was acquired from the Taconic Laboratory (Germantown, N.Y.). Both mouse strains were bred and maintained under standard conditions at The Wistar Institute (Philadelphia, Pa.). These mice and their relative ability to heal wounds are described in Desquenne Clark et al. *Clin. Immunol. Immunopathol.* 88, 35–45, 1998.

Antibodies. Primary antibodies against PCNA (mMab; NA03; Calbiochem), Ki-67 (mMab; NCL-Ki67-MM1; Novacastra Labs Ltd), BrdU (mMab Fab2; 1585 860; Boehringer Mannheim), sarcomeric α-actinin (mMab; A7811; Sigma), α-smooth muscle actin (mMab; IMMH-2; Sigma), FGF-2 (sc-79-G; Santa Cruz Biotech; CA), caspase 3 (rabbit; AF835; R&D Systems, Inc), BC1-2 (rabbit; PC68; Oncogene), were used for immunohistochemistry. Secondary antibodies used included biotin conjugates of donkey-anti-mouse, donkey-anti rabbit IgG and donkey-anti-goat IgG (Jackson Immunoresearch), and biotin-mouse anti-rabbit IgG (Sigma).

BrdU treatment. BrdU was obtained from Boehringer Manheim and was injected at a dosage of 150 mg/kg.

Cardiac injury. Myocardial injury is cryogenically initiated, employing a technique adapted from Taylor et al. (1998) (ref 28). Adult MRL and C57B1/6 mice (6–8 weeks of age) were anaesthetized using an intraperitoneal injection of ketamine (100 mg/kg) and xylazine (15 mg/kg). A 2 mm diameter blunt probe cooled to the temperature of liquid Nitrogen is then introduced, trans-diaphragmatically, to the right ventricular surface of the heart. Injury thus induced precludes complications inherent to a thoracic approach to the heart and has the following advantages: eliminates the need for artificial ventilation, does not compromise the pneumothorax, reduces the overall extent of trauma in tissues in vicinity to the heart and adjacent thoracic structures and organs, co-induces an injury to the diaphragm, a striated, skeletal muscle, with which to compare the responses of the two, distinct striated muscle types to injury and their subsequent regenerative processes.

Access to the diaphragm was accomplished by a 6–8 mm incision made through the skin on the ventral surface of the abdomen below the ribcage approximately 5 mm posterior to—and approximately 5 mm to the left of the ventral midline—the sternum. The underlying musculature was incised to an equivalent extent. The diaphragm was exposed using forceps to retract the medial lobe of the liver. The right ventricular surface of the heart was thus presented directly adjacent to, and clearly visible through, the diaphragm. Injury to the heart was achieved by holding the cryoprobe in contact with the diaphragmatic surface for 10 seconds and repeated using a second, identical cryoprobe. The abdominal musculature was then repositioned and closed using 6-0 absorbable suture. The 6-0 nylon suture was also used for skin closure.

Histology Frozen sections: Hearts were removed and frozen in isopentane cooled to −160° C. in liquid nitrogen. Eight micron-thick sections were cut for immunohistochemistry and histology. Fixed sections: Hearts were fixed in Prefer Fixative (Anatheh Ltd.). Paraffin-embedded sections cut to a thickness of 5 microns were used for both histology and immunohistochemistry.

EXAMPLE 2

Cardiac Muscle Regeneration in MRL Mice

Adult healer (MRL/+) and non-healer (C57B1/6) mice (6–8 weeks of age) were anaesthetized using an intraperitoneal injection of ketamine (100 mg/kg) and xylazine (15 mg/kg). Myocardial injury was then cryogenically initiated. A 2 mm diameter blunt probe cooled to the temperature of liquid Nitrogen was then introduced, trans-diaphragmatically, to the right ventricular surface of the heart. Injury thus induced precluded complications inherent to a thoracic approach to the heart and had the following: it eliminated the need for artificial ventilation, it did not compromise the pneumothorax, it reduced the overall extent of trauma in tissues in vicinity to the heart and adjacent thoracic structures and organs, and it co-induced an injury to the diaphragm, a striated, skeletal muscle, with which to compare the responses of the two distinct striated muscle types to injury and their subsequent regenerative processes.

Access to the diaphragm was accomplished by a 6–8 mm incision made through the skin on the ventral surface of the abdomen below the ribcage approximately 5 mm posterior to the sternum and approximately 5 mm to the left of the ventral midline. The underlying musculature was incised to an equivalent extent. The diaphragm was exposed using forceps to retract the medial lobe of the liver. The right ventricular surface of the heart was thus presented directly adjacent to, and clearly visible through, the diaphragm. Injury to the heart was achieved by holding the cryoprobe in contact with the diaphragmatic surface for 10 seconds and was repeated, using a second, identical cryoprobe. The abdominal musculature was then repositioned and closed using 6-0 absorbable suture. 6-0 nylon suture is used for skin closure.

The tissue was examined at days 7, 15, 60, and 90. The hearts and diaphragms were removed, frozen or fixed, and embedded in paraffin. Serial sections were made around the wound site and stained with hematoxylin and eosin or with trichrome stain.

On day 7, the cardiac wound site in both the healer and the non-healer densely filled in with fibroblast-like cells. The non-healer showed a highly disorganized and porous tissue structure with necrotic areas and ghost-like nonvital cardiomyocytes. The healer presented as organized tissue composed of tightly packed and aligned fibroblasts in intimate contact with normal unwounded cardiac muscle tissue. Areas of finger-like muscle fiber protruded into the wound site. These protrusions were found to be positive for the heart-specific muscle antigen, α-actinin.

On day 15, cardiac tissue in the healer mouse showed muscle filling the wound site with little evidence of fibrosis or scar tissue. A thin line of fibroblast-like cells lined up along the muscle: In the nonhealer mouse, the wound consisted of damaged muscle remnants, interspersed with muscle which looked like it had originally not died off, interspersed with fibrotic tissue which appears to have replaced the wounded muscle.

By day 60, the healer heart looked normal and remained so up to day 90. The nonhealer heart showed scar tissue and never changed with time. BrdU studies indicated that cardiomyocytes had divided in the MRL mice.

One of the most striking differences between the two types of mice is that epithelial cells surrounding the heart in the MRL mice proliferated early on, surrounding the wound and appearing to protect it. This was not so in the B6 mice; thus, tissue breakdown and fibrosis occurred.

EXAMPLE 3

Cardiac Muscle Regeneration in B6 Congenic Mice

B6 congenic mice, which contain approximately 98% nonhealer B6 genes and 2% healer MRL genes, have been shown to heal ear hole wounds. McBrearty et al., *Proc. Natl. Acad. Sci. U.S.A.* 95, 11792–97, 1998. These mice then received a cryo-injury of the heart. Analysis of two such animals showed that on day 15, healing was more similar to that in the MRL mouse than the B6 mouse. In fact, healing was even better than that in the MRL mouse. This is similar to what has been found in the ear, where wounds in the B6 congenic mouse heal better than those in the original MRL healer mouse.

This result indicates that the genes that have been selected in the B6 congenic mice for the healing of ear hole wounds include genes that are involved in healing of heart tissue.

EXAMPLE 4

Cardiac Muscle Regeneration in C57B1/6 Mice after Treatment with Propylthiouracil Molecules made by the thyroid gland have a particular and important function in amphibians; they are involved in the metamorphosis of tadpoles adult frogs. If the thyroid gland is removed from a developing tadpole embryo, the tadpole never becomes a frog. If thyroid hormone is injected, the tadpole transforms more rapidly into a frog. Importantly, if an anti-thyroid drug such as propylthiouracil (PTU) is injected into a tadpole, it never metamorphoses into a frog.

Interestingly, the tadpole can regenerate tissue while the frog cannot. When thyroid hormone rises in the tadpole stage, new muscle fibers arise by cell division. At a slightly later timepoint, fibers degenerate and are removed by phagocytes. When thyroid hormone peaks, no new fibers appear, but muscle grows by hypertrophy. Another key event is rapid re-epithelialization. This occurs in the tadpole but disappears in the frog, again a function of thyroid hormone.

Rapid re-epithelialization seems to be an important event in regeneration in amphibians in general. Rapid re-epithelialization occurs in the ears of MRL mice after injury and also in the MRL heart after injury.

To determine whether thyroid hormone is reduced in MRL compared to B6 mice, we bled mice (4 MRL, 5 B6) and determined the levels of T3 and T4. The normal range for T3 levels is 65–138 ng/dl. The adjusted T3 level for B6 mice was 134 ng/dl; for MRL mice, the adjusted T3 level was 94.5 ng/dl. Thus, the T3 level in the MRL mouse is lower than in the B6 mouse.

The normal range for T4 (thyroxin levels is 3.5–7.4 $\mu$g/dl. The adjusted T3 level for B6 mice was 6.6 $\mu$g/dl and for MRL mice was 3.3 $\mu$g/dl.

These experiments demonstrated that MRL mice had significantly lower levels of functional thyroid hormone than B6 mice.

To determine whether administering T3 to MRL mice inhibits healing of ear and heart wounds, we placed pellets containing 0.01 mg of T3 in a slow release formulation (21 days) in MRL mice. Via these pellets, the mice received 0.0005 mg/day of T3. Mice were injured one day later. By day 15, the MRL hearts were severely scarred, with a large degree of fibrotic tissue (reminiscent of the B6 mouse), and the MRL hearts never healed.

We also treated nonhealer C57B1/6 mice with PTU, which is known to inhibit thyroid activity. Wounded C57B1/6 mice pretreated with PTU showed significantly greater growth of myocardium, with a more intact epithelial layer, than untreated C57B1/6 mice (FIG. 1). Providing mice with larger concentrations of PTU (2 or 3 mg/day) resulted in better healing and greater epithelial growth.

EXAMPLE 5

Ear Hole Closure in C57B1/6 Mice after Treatment with PTU

An ear hole wound in a B6 mouse 15 days after PTU treatment showed an impressive degree of epithelial proliferation, as well as muscle and adipocyte proliferation. Ear holes were smaller than that seen in the untreated B6 ear holes.

EXAMPLE 6

Figure 1B:
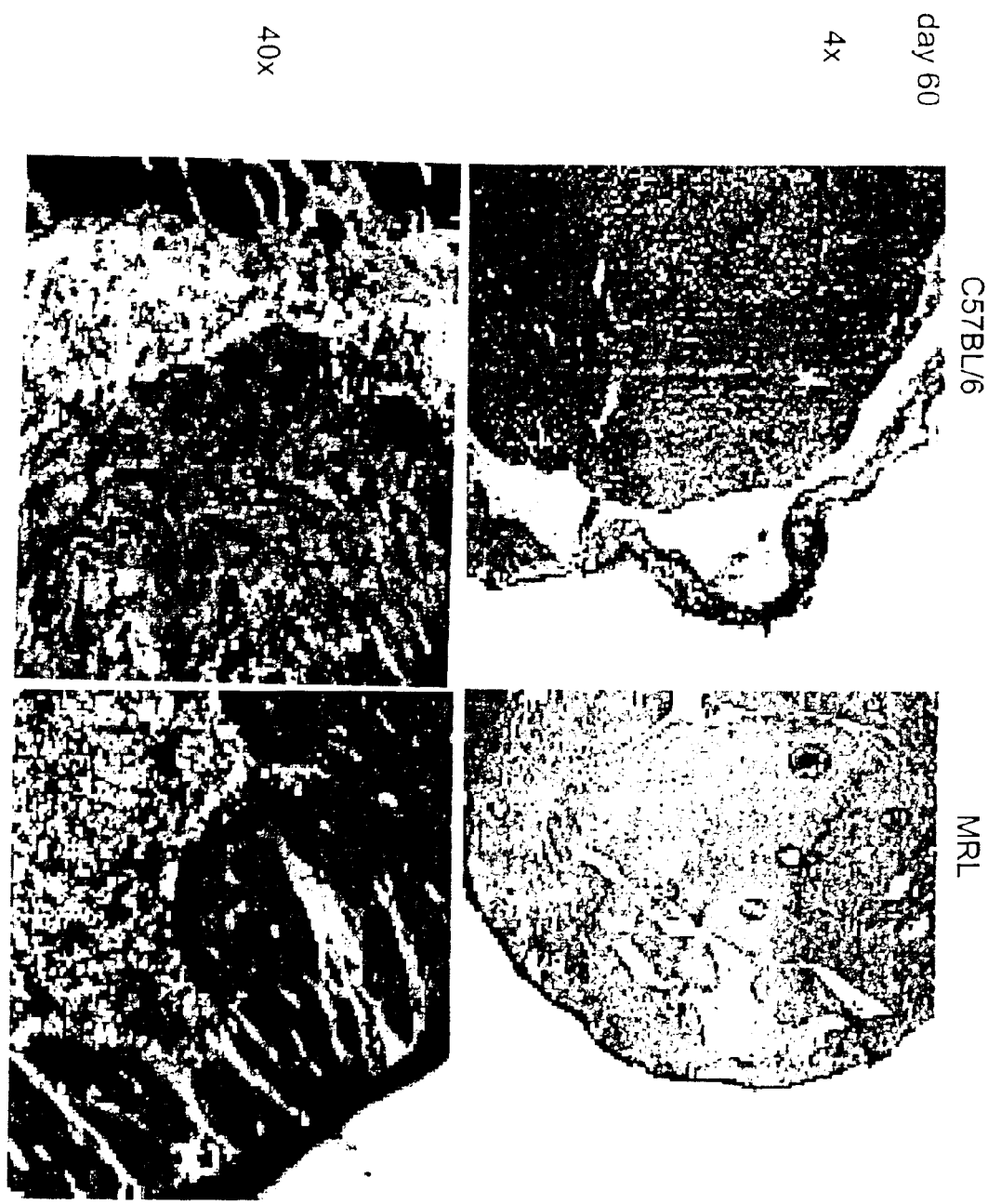

Using a method of cardiac injury which involved no surgical entry into the thoracic cavity but which instead created a wound on the right ventricle of the heart across the diaphragm using a cold probe, we injured C57B1/6 (nonhealer) and MRL (healer) mice and then followed these injuries for up to 60 days (days 1–5,7,15 and 60). Several major differences were seen (FIG. 1). First, the C57B1/6 hearts showed a large number of fibroblast-like cells which appeared from day 2 and remained as a disorganized mass of cells. On the other hand, the MRL wound filled with fibroblast-like cells one day later (day 3) than the C57B1/6 heart and appeared much more organized from day 3 onward (FIG. 1A). The C57BL/6 injury had a lacy appearance up to day 15, whereas the MRL wound continued to fill with muscle-like cells. By day 60 (FIG. 1B), the area of the C57B1/6 heart which was wounded was now filled with scar tissue whereas the MRL heart appeared essentially normal.

Second, the tri chrome stain approximated the amount and location of collagen present and it was clear that there was a major difference between the two strains. Small patches of collagen could be seen in the C57B1/6 wound throughout the healing period without evidence of organization of what little collagen was present. At later time points a collagen layer was deposited between the fibroblast and muscle layer. Organized collagen fibers could be seen in the MRL wound on day 3 and continued to increase, being laid down between lined up fibers (FIG. 1A).

Figure 2:
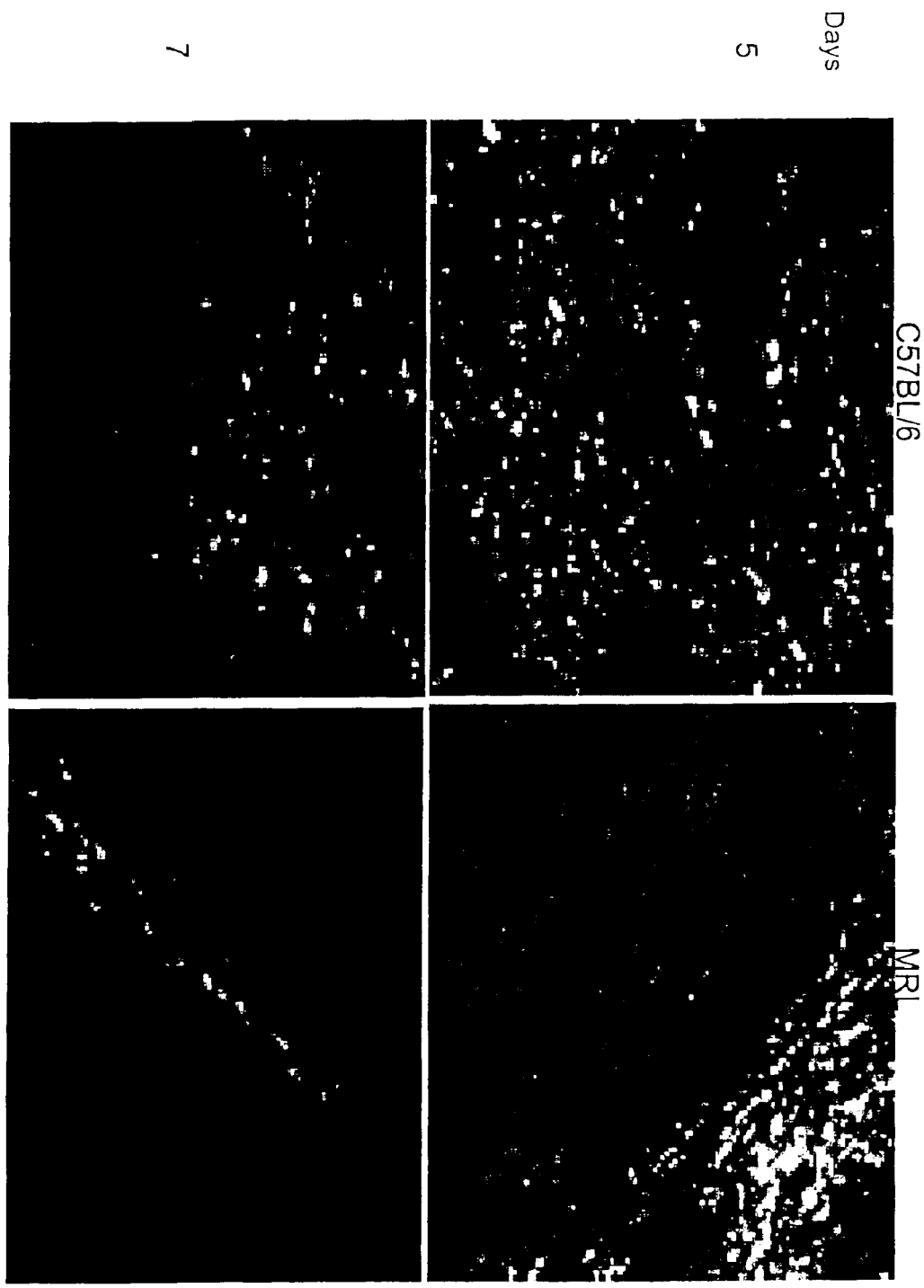
FIG. 2. Cardiac tissue from C57B1/6 and MRL mice injected with BrdU was removed at various days 5 and 7 after cryo-injury and quick-frozen. Frozen sections were then stained with fluorescent anti-BrdU and visualized with a fluorescent microscope.

To determine whether the cells in the wound included proliferating cells and were not due to migrating cells, mice were injected with BrdU at the time of wounding and frozen sections were examined with fl-anti-BrdU antibody on days 5 and 7. It is clear that the cells in the wound are positive for BrdU (FIG. 2), though there is a striking difference between the C57B1/6 and MRL. Confirming the results described above, the C57B1/6 maintains a disorganized group of dividing cells in the wound whereas the MRL shows two distinct populations of dividing cells, one disorganized which disappears with time and one highly organized and found lined up next to the pre-existing normal heart tissue.

Figure 3:
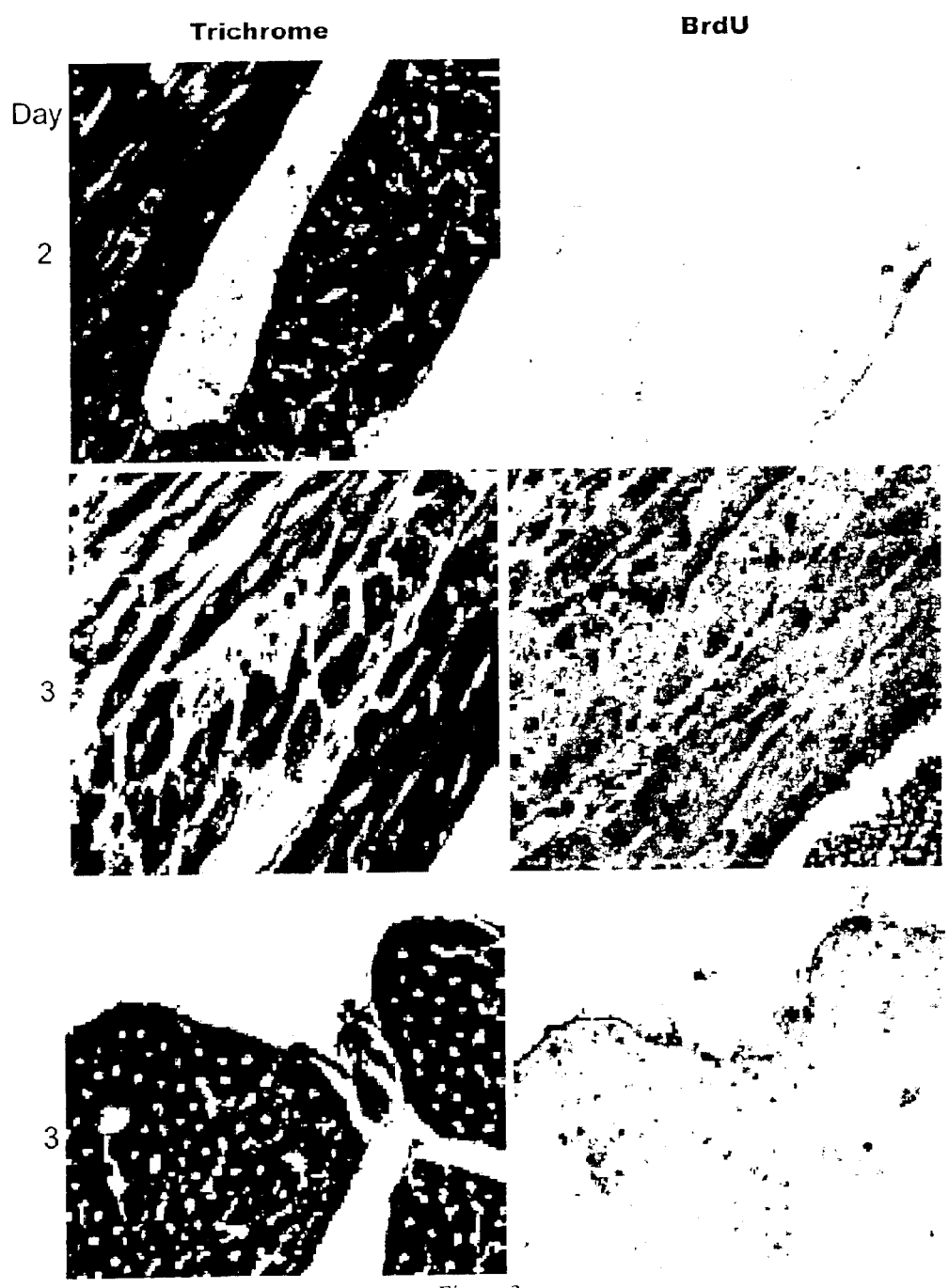
FIG. 3. Cardiac tissue from C57B1/6 and MRL mice injected once with BrdU was removed at days 2 and 3 after cryo-injury and then fixed in Prefer solution, paraffin imbedded, sectioned and either stained with trichrome or with anti-BrdU and developed with DAB. Dividing nuclei of myocardial cells seen with trichrome are shown to be labeled with BrdU, indicating cell division.
Figure 4:
FIG. 4. Cardiac tissue from C57B1/6 and MRL mice injected once with BrdU was removed at days 2 and 3 after cryo-injury and then fixed in Prefer solution, paraffin imbedded, sectioned and either stained with trichrome or with anti-BrdU and developed with DAB. Dividing nuclei of myocardial cells seen with trichrome are shown to be labeled with BrdU, indicating cell division. Here, the division of epithelial cells can be seen in the MRL.
Figure 5:
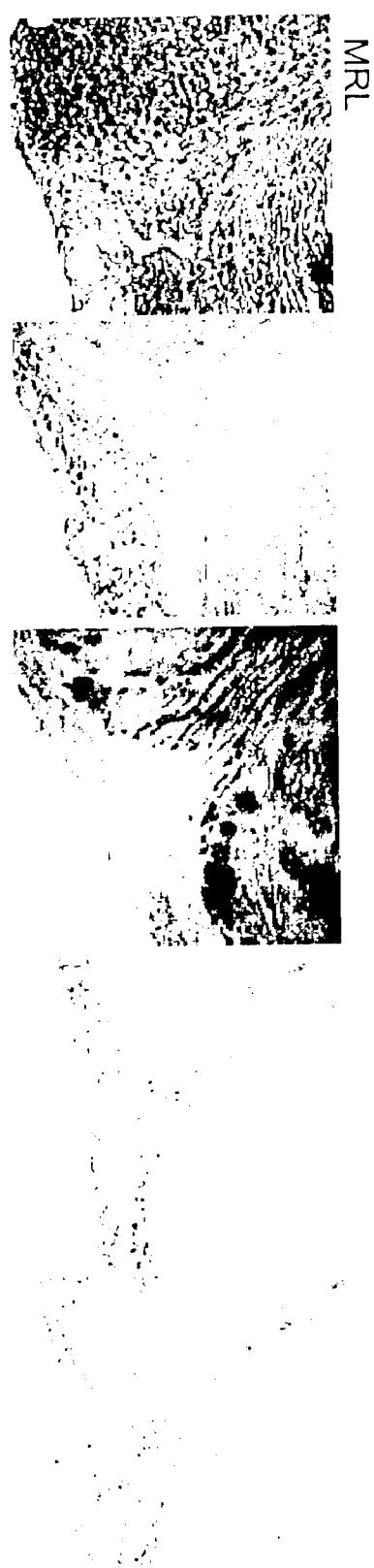
FIG. 5. Cardiac tissue from C57B1/6 and MRL mice injected once with BrdU was removed at days 2 and 3 after cryo-injury and then fixed in Prefer solution, paraffin imbedded, sectioned and either stained with trichrome or with anti-BrdU and developed with DAB. Dividing nuclei of myocardial cells seen with trichrome are shown to be labeled with BrdU, indicating cell division. Here, serial sections of cardiac tissue from day 7 after injury have been stained with H&E, anti-BrdU, anti-α-actinin, Ki-67, and anti-PCNA antibodies.
Figure 5:

Close examination of the heart early after wounding showed fibers proximal but not distal to the wound that bad multiple nuclei predominantly in the MRL. Immunohistochemical staining (FIG. 3A,B) with anti-BrdU showed positive nuclei as early as day 1 after wounding, increasing by day 3 with positive nuclei also distal to the wound. Besides evidence of dividing myocardial cells, it became clear that the pericardial layer was proliferating extensively in the MRL on day 2, unlike the C57B1/6 which showed only a small degree of proliferation and coverage (FIG. 4). By day 7, significant BrdU staining could be found in areas positive for α-actinin, again predominantly in the MRL. Since BrdU was given only at the time of wounding, evidence for recently dividing cells was determined by staining with anti-PCNA and anti-Ki-67 antibodies. In the C57B1/6 wound, no evidence of recent cell division was seen in the a-actinin positive areas. In the MRL wound, new cell division was seen in the α-actinin-positive area and was colocalized with the BrdU staining (FIG. 5). This indicated that cell division in the MRL was ongoing. BrdU was then injected every 5 days at wounded tissue was examined at 15 days (FIG. 6).

Discussion

In the present study, we used in the mouse the same cryoinjury model previously described in the rabbit (14,18, 19). In the two strains of mice examined, the C57B1/6 mouse and the MRL mouse, a defect in the right ventricle of the heart was produced. Cardiocytes died within the first three days and fibroblasts and inflammatory cells filled the wound. However, beyond that, the response of the two strains was quite different. In the B6 mouse, the infiltrating cells produced a mass of highly disorganized tissue with sparse amounts of collagen, most of it laid down around the new connective tissue, both at margin of healthy muscle and the surface of the heart. There was little evidence of cardiomyocytes in the zone of healing. In contrast to this, the MRL infiltrating cells produced a well organized tissue mass composed of α-actinin-positive cardiomyocytes, with collagen being laid down between the cell layers and not in large amounts at any given surface. On possible reason is the rapid proliferative response of the epithelial layer seen in the MRL mouse.

Thus, the C57B1/6 mouse healing capacity was similar to that seen in the rabbit. Interestingly, the rabbit has been considered an animal which displays unusual regenerative properties. It bad been found that through and through ear punches healed with the regeneration of new cartilage and no scarring. In fact, it displayed the same kind of ear hole closure as the MRL mouse (16,20). Given the results presented here, the MRL mouse is not identical to the rabbit but rather appears to have an even greater capacity for regeneration than the rabbit.

The regeneration of muscle is seen in the mammal as well as in the amphibian but only certain elements are shared. In both cases satellite cells in striated muscle act as stem cells which can replace mature muscle. However, in the amphibian, DNA synthesis can occur in mature multinucleated fibers where it does not occur in mammals. Molecules involved in the cell cycle and specifically in the G1/S phase have been closely examined. Differences in retinoblastoma protein (Rb) phosphorylation, the presence of p107 and 130, cyclin D, and cdk2 have been seen expressed in adult amphibian but not mammalian myofibers (3). In an effort to recreate the conditions for cell division in mammals, various transgenics have given some indication that the G1 checkpoint might be overcome in mammals (21–23). However, the difference between mammals and amphibians may very well be upstream of Rb.

REFERENCES

1. Lo er al., 1993. Reversal of muscle differentiation during urodele limb regeneration. PNAS 90:7230–7234.
2. Tanaka et al., 1997. Newt myotubes reenter the cell cycle by phosphorylation of the retinoblastoma protein. Journal of Cell Biology. 136(1):155–65.
3. Tanaka et al., 1999. Thrombin regulates S-phase reentry by cultured newt myotubes. Current Biology 9:692–799.
4. Corcoran & Ferretti, 1999. RA regulation of keratin expression and myogenesis suggests different ways of regenerating muscle in adult amphibian limbs. Journal of Cell Science. 112: 1385–94.
5. Koishi et al., 1995. MyoD protein accumulates in satellite cells and is neurally regulated in regenerating myotubes and skeletal muscle fibers. Developmental Dynamics. 202: 244–54.
6. Rumyantev, 1973. Post-injury DNA synthesis, mitosis, and ultrastructural reorganization of adult frog cardiac myocytes. Z. Zellforsch. 139: 431–450.
7. Oberpriller et al., 1985. Activation of DNA synthesis and mitotic events in atrial myocytes following atrial and ventricular injury. In Pathobiology of Cardiovascular Injury. (Stone and Weglicki, eds) Martinus Nijhoff Publishing, Boston. p. 410–421.
8. Nadal-Ginard, B. 1978. Commitment, fusion, and biochemical differentiation of a myogenic cell line in the absence of DNA synthesis. Cell. 15:855–864.
9. Carbone et al., 1995. Hamster Cardiomyocytes: a model of myocardial regeneration ? Annals of the New York Academy of Sciences.752:75–91
10. Soonpaa et al., 1994 Formation of nascent intercalated disks between grafted cardiomyocytes and most myocardium. Science 264: 98–101.
11. Klug et al., 1996, Genetically selected cardiomyocytes from differentiating embryonic stem cells form stable intracardiac grafts. J. Clin. Invest 98: 216–224.
12. Marelli et al., 1992, Cell transplantation for myocardial repair: an experimental approach. Cell Transplant. 1:383–390.
13. Robinson, SW, 1996 Arterial delivery of genetically labelled skeletal myoblasts to the murine heart: long term survival and phenotypic modification of implanted myoblasts. Cell transplant. 5: 77–91.
14. Taylor et al., 1998. Regenerating functional myocardium: improved performance after skeletal myoblast transplantation. Nature Medicine 4:929–933.
15. Silvestry S. C., 1996, The in vivo quantification of myocardial performance in rabbits: a model for evaluation of cardiac gene therapy. J. Mol. Cell. Cardiol.28: 815–823.
16. Desquenne Clark et al., 1998 A New Murine Model for Mammalian Wound Repair and Regeneration. Clinical Immunology and Immunopathology. 88: 35–45.
17. McBrearty et al., 1998 Genetic analysis of a mammalian wound-healing trait. Proc. Natl Acad. Sci. 95:11792–11797.
18. Gill et al., 1970 The control and predictability of a cryolesion. Cryobiol. 6: 347–353.
19. Gill, W. and Long W. B. (1971). The completeness of cellular destruction within a cryolesion. Brit. J. Surg. 58:870.
20. Goss & Grimes, 1975. Epidermal downgrowths in regenerating rabbit ear holes. J. Morphology. 146: 533–42.
21. Soonpaa et al., 1997. Cyclin Dl overexpression promotes cardiomyocyte DNA synthesis and multinucleation in transgenic mice. Journal of Clinical Investigation. 99:2644–54.
22. Hassankhani et al., 1995. Overexpression of NGF within the heart of transgenic mice causes hyperinnervation, cardiac enlargement, and hyperplasia of ectopic cells. Developmental Biology (Orlando). 169(1):309–21.
23. Koh et al., 1995. Targeted expression of transforming growth factor-beta 1 in intracardiac grafts promotes vascular endothelial cell DNA synthesis. Journal of Clinical Investigation. 95(1): 114–21.
24. Gross, J. Getting to mammalian wound repair and amphibian limb regeneration: a mechanistic link in the early events. *Wound Repair and Regeneration* 4,190–202, 1996.
25. Michalopoulos & DeFrances, Liver Regeneration. *Science* 276, 60–66, 1997.
26. Potten & Morris, Epithelial stem cells in vivo. In Stem Cells. (eds. Lord, B. I. and Dexter, T. M.) pp. 45–62, The Company of Biologists Limited, Cambridge, 1988.
27. Spangrude et al., Purification and characterization of mouse hematopoietic stem cells. *Science* 241, 58–62, 1988.
28. Clark, R. A. F. Wound Repair: Overview and general considerations. In The Molecular and Cellular Biology of Wound Repair. (ed. Clark, R.) pp. 3–35, Plenum Press, New York, 1996.

What is claimed is:

1. A method of increasing healing of a heart wound in a euthyroid adult mammal, comprising the step of administering to a first euthyroid adult mammal having a heart wound an amount of propylthiouracil effective to decrease a level of a T3 or T4 thyroid hormone relative to the T3 or T4 thyroid hormone level in a second euthyroid adult mammal to whom the thyroid hormone-lowering agent has not been administered, whereby healing of a heart wound in the first euthyroid adult mammal is increased relative to healing of a heart wound in the second euthyroid adult mammal.

2. A method of increasing healing of a heart wound in a euthyroid adult C57B1/6 mouse, comprising the step of administering to a first euthyroid adult C57B1/6 mouse having a heart wound an amount of a thyroid hormone-lowering agent effective to decrease a level of a T3 or T4 thyroid hormone relative to the T3 or T4 thyroid hormone level in a second euthyroid adult C57B1/6 mouse to whom the thyroid hormone-lowering agent has not been administered, whereby healing of a heart wound in the first euthyroid adult C57B1/6 mouse is increased relative to healing of a heart wound in the second euthyroid adult C57B1/6 mouse.

3. The method of claim 1 wherein the first and second euthyroid adult mammals are humans.

4. A method of increasing healing of a heart wound in a euthyroid adult mammal, comprising the step of administering to a first euthyroid adult mammal having a heart wound an amount of a thyroid hormone-lowering agent effective to decrease a level of a T3 or T4 thyroid hormone relative to the T3 or T4 thyroid hormone level in a second euthyroid adult mammal to whom the thyroid hormone-lowering agent has not been administered, whereby healing of a heart wound in the first euthyroid adult mammal is increased relative to healing of a heart wound in the second euthyroid adult mammal, wherein the increased healing in the first euthyroid adult mammal comprises re-epithelialization.

5. A method of increasing healing of a heart wound in a euthyroid adult mammal, comprising the step of administering to a first euthyroid adult mammal having a heart wound an amount of a thyroid hormone-lowering agent effective to decrease a level of a T3 or T4 thyroid hormone relative to the T3 or T4 thyroid hormone level in a second euthyroid adult mammal to whom the thyroid hormone-lowering agent has not been administered, whereby healing of a heart wound in the first euthyroid adult mammal is increased relative to healing of a heart wound in the second euthyroid adult mammal, wherein the thyroid hormone lowering agent decreases T4 levels.

6. The method of claim 1 wherein the heart wound is an ischemic infarct.

7. A method of increasing healing of a heart wound in a euthyroid adult mammal, comprising the step of administering to a first euthyroid adult mammal having a heart wound an amount of a thyroid hormone-lowering agent effective to decrease a level of a T3 or T4 thyroid hormone relative to the T3 or T4 thyroid hormone level in a second euthyroid adult mammal to whom the thyroid hormone-lowering agent has not been administered, whereby healing of a heart wound in the first euthyroid adult mammal is increased relative to healing of a heart wound in the second euthyroid adult mammal, further comprising the step of detecting increased healing of the heart wound in the first euthyroid adult mammal.

8. A method of increasing healing of a heart wound in a euthyroid adult mammal, comprising the step of administering to a first euthyroid adult mammal having a heart wound an amount of a thyroid hormone-lowering agent effective to decrease a level of a T3 or T4 thyroid hormone relative to the T3 or T4 thyroid hormone level in a second euthyroid adult mammal to whom the thyroid hormone-lowering agent has not been administered, whereby healing of a heart wound in the first euthyroid adult mammal is increased relative to healing of a heart wound in the second euthyroid adult mammal, wherein the level of the T3 or T4 thyroid hormone is decreased by at least 90% relative to the T3 or T4 thyroid hormone level in the second euthyroid adult mammal.

9. The method of claim 8 wherein the level of the T3 or T4 thyroid hormone is decreased by at least 95% relative to the T3 or T4 thyroid hormone level in the second euthyroid adult mammal.

10. The method of claim 8 wherein the level of the T3 or T4 thyroid hormone is decreased by at least 99% relative to the T3 or T4 thyroid hormone level in the second euthyroid adult mammal.

11. The method of claim 8 wherein the level of the T3 or T4 thyroid hormone is decreased by at least 100% relative to the T3 or T4 thyroid hormone level in the second euthyroid adult mammal.

* * * * *